US00RE34761E

United States Patent [19]

Dafinger et al.

[11] E Patent Number: Re. 34,761

[45] Reissued Date of Patent: Oct. 18, 1994

[54] PROCESS FOR THE PREPARATION OF TRICHLOROETHYLENE

[75] Inventors: Willibald Dafinger, Emmerting; Wolfdietrich Gabler, Burghausen; Eduard Pichl, Burghausen; Roman Hierzegger, Burghausen, all of Fed. Rep. of Germany

[73] Assignee: Wacker-Chemie GmbH, Munich, Fed. Rep. of Germany

[21] Appl. No.: 138,463

[22] Filed: Oct. 15, 1993

Related U.S. Patent Documents

Reissue of:

[64] Patent No.: 5,091,603
Issued: Feb. 25, 1992
Appl. No.: 602,417
Filed: Oct. 22, 1990

[30] Foreign Application Priority Data

Dec. 12, 1989 [DE] Fed. Rep. of Germany ..... 3941037

[51] Int. Cl.[5] ..... C07C 17/34
[52] U.S. Cl. ..... 570/230; 570/189
[58] Field of Search ..... 570/230, 189, 176

[56] References Cited

FOREIGN PATENT DOCUMENTS 3804265 2/1988 Fed. Rep. of Germany .

*Primary Examiner*—Johann Richter
*Assistant Examiner*—Kimberly J. Kestler
*Attorney, Agent, or Firm*—Burgess, Ryan and Wayne

[57] ABSTRACT

In the process, a copper/rhodium catalyst impregnated with 0.1 to 10.0% by weight, based on the total weight of active charcoal catalyst support and active components, of a water-soluble phosphonium halide is employed for the preparation of trichloroelethylene from perchloroethylene and hydrogen.

12 Claims, 1 Drawing Sheet

PROCESS FOR THE PREPARATION OF TRICHLOROETHYLENE

Figure 1:
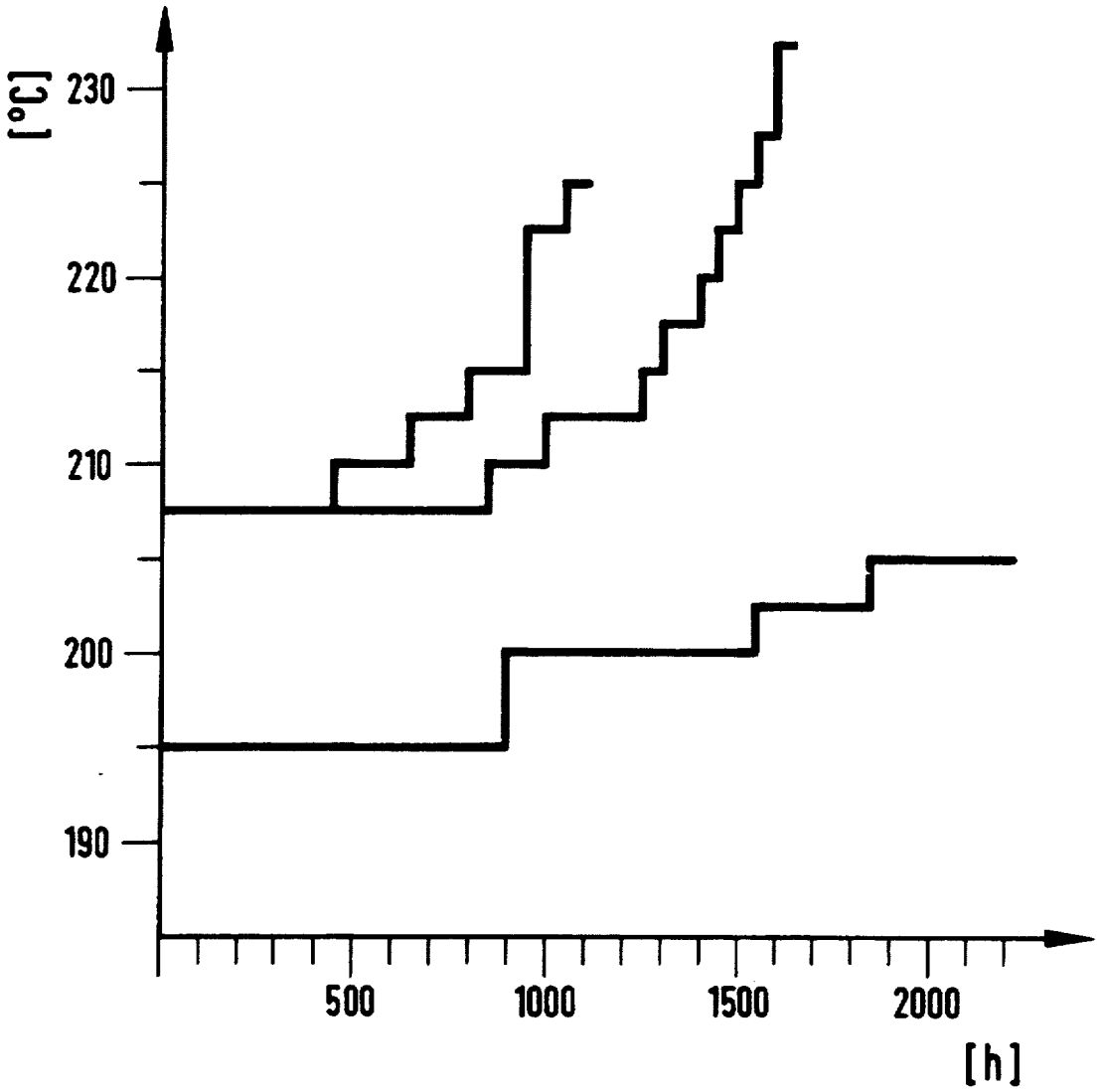

Matter enclosed in heavy brackets [ ] appears in the original patent but forms no part of this reissue specification; matter printed in italics indicates the additions made by reissue.

FIELD OF THE INVENTION

The invention relates to a process for the preparation of trichloroethylene from perchloroethylene and hydrogen by means of a copper/rhodium catalyst impregnated with a water-soluble phosphonium halide.

BACKGROUND OF THE INVENTION

A process for preparing trichloroethylene from perchloroethylene and hydrogen in which a catalyst consisting of an active charcoal support impregnated with copper in elemental or chemically bonded form and palladium, rhodium or ruthenium, in each case in elemental or chemically bonded form, is employed, is known from DE-A 2,819,209 (EP-B 5,263). The high temperatures which are required to obtain satisfactory conversion rates are a disadvantage of this procedure.

To increase the catalyst activity at a lower reaction temperature, DE-A 3,804,265 proposes the use of copper/rhodium catalysts impregnated with phosphines or phosphites. The fact that, in an expensive two-stage process for impregnation of the catalyst support, the aqueous solution of the copper compound and rhodium compound first has to be applied, and in the following step the phosphines or phosphites dissolved in organic solvents have to be applied is a disadvantage of this procedure. Above all, however, the increase in catalyst activity is limited with respect to time, so that the drop in activity after operating times of less than only 1000 hours must be counteracted by an increase in the operating temperature.

The object of the present invention was thus to provide a process for the preparation of trichloroethylene from perchloroethylene and hydrogen, with which high conversions can be achieved even at a relatively low operating temperature, even over long operating times.

SUMMARY OF THE INVENTION

The invention relates to a process for the preparation of trichloroethylene from perchloroethylene and hydrogen by means of a supported catalyst consisting of active charcoal having a BET surface area of more than 500 $m^2/g$, 0.5 to 20% by weight of copper in elemental or chemically bonded form and 0.01 to 1.0% by weight of rhodium or palladium in elemental or chemically bonded form at a temperature of 150° to 250° C. and a hydrogen pressure of 1 to 10 bar absolute, wherein the supported catalyst is impregnated with 0.1 to 10.0% by weight of a water-soluble phosphonium halide.

Active charcoal, preferably in granular form, having a BET surface area of more than 500 $m^2/g$ and a particle size of 2 to 10 mm is employed as the catalyst support.

The copper is applied to the support in elemental or chemically bonded form in amount of 0.5 to 20.0% by weight, preferably 5.0 to 15.0% by weight, based on the total weight of catalyst support and active components.

Water-soluble copper salts, in particular $CuCl_2$, are particularly preferred.

Rhodium is employed in elemental or chemically bonded form in an amount of 0.01 to 1.0% by weight, preferably 0.02 to 0.2% by weight, based on the total weight of catalyst support and active components. Water-soluble rhodium compounds, in particular complex salts of rhodium(III) chloride, are particularly preferred. Instead of rhodium, it is also possible to employ palladium in elemental or chemically bonded form and in the amounts just stated for rhodium. Water-soluble palladium compounds, such as, for example, $PdCl_2$, are also particularly preferred here.

According to the invention, the catalyst support is also impregnated with 0.1 to 10.0% by weight, preferably 3.0 to 7.0% by weight, based on the total weight of catalyst support and active components, of a water-soluble phosphonium halide. Water-soluble phosphonium halides of the general formula $(Ph_3PR)X$ are preferably employed; wherein Ph represents a phenyl radical.

R represents hydrogen or substituted or unsubstituted alkyl or aryl radicals. Examples of these are the methyl, ethyl, propyl, n-butyl, iso-butyl, pentyl, hexyl, heptyl, octyl, nonyl, benzyl, p-chlorobenzyl, p-tert.butylbenzyl, allyl, 2-methyallyl, chloromethyl, dichloromethyl, iodomethyl, ethoxycarbonylmethyl and acetonyl radicals.

Chloride, iodide or bromide is preferably employed as the halide X.

Preferred phosphonium halides are methyltriphenylphosphonium chloride, methyltriphenylphosphonium bromide, ethyltriphenylphosphonium chloride, ethyltriphenylphosphonium bromide, n-propyltriphenylphosphonium chloride, n-propyltriphenylphosphonium bromide, allyltriphenylphosphonium chloride, allytriphenylphosphonium bromide, n-butyltriphenylphosphonium chloride and n-butyltriphenylphosphonium bromide.

Methyltriphenylphosphonium chloride, methyltriphenylphosphonium bromide, ethyltriphenylphosphonium chloride and ethyltriphenylphosphonium bromide are particularly preferred.

The phosphonium halides can be prepared in a manner which is known per se. For example, the triphenylphosphonium salts are obtained by the reaction of triphenylphosphine with the corresponding hydrogen halide compounds. If the optionally substituted alkyl halides are employed, the alkyl-triphenylphosphonium salts are accessible. Further procedures for the preparation of phosphonium halides are described in the following publications: J. Buddrus, Chem. Ber. 107, 2062 (1974); G. Wittig, U. Schöllkopf, Chem. Ber. 87, 1318 (1954); D. Denney, L. Smith, J. Org. Chem. 45, 3404 (1962); G. Wittig, M. Schlosser, Chem. Ber. 94, 1373 (1961); G. Aksnes, A. Eide, Phosphorus 4 (3), 209 (1974); Houben-Weyl, Methoden der organischen Chemie (Methods of organic chemistry) 12/1, 79 (1963); and Ullmann, Encyclopädie der technischem Chemie (Encyclopedia of industrial chemistry) 18, 380 (1979).

For the impregnation, the individual components, that is to say copper (salt), rhodium (salt) or palladium (salt) and phosphonium compound, preferably in aqueous solution, are applied to the active charcoal separately or as a mixture, for example by steeping. The catalyst support impregnated in this way is then dried.

For reaction of the perchloroethylene, the catalyst is introduced in poured form into a reaction tube. The reaction is carried out at a temperature of 150° to 250°

C. and under a pressure of 1 to 10 bar absolute. The perchloroethylene is preferably reacted in amounts of 0.5 to 5.0 mol per hour and per liter of contact mass (catalyst volume) together with 0.1 to 1 times the molar amount per hour of hydrogen.

The following examples serve to further illustrate the invention:

EXAMPLE 1

Granular active charcoal having a BET surface area of 800 $m^2/g$ and a particle size of 3 mm (Degusorb WS IV Spezial, Degussa) was steeped with aqueous solutions of $CuCl_2$, $Na_3RhCl_6$ and $[(C_6H_5)_3PCH_3]Cl$ and then dried, so that the Cu content of the active charcoal was 10% by weight, the Rh content was 0.044% by weight and the $[(C_6H_5)_3PCH_3]Cl$ content was 6.5% by weight. The trichloroethylene preparation was carried out in a single-tube reactor using a catalyst volume of 1500 ml. The reactor was charged with 960 g/hour (5.8 mol/hour) of perchloroethylene and 70 l/hour (3.5 mol/hour) of hydrogen. The reaction pressure was 6 bar absolute.

COMPARISON EXAMPLE 1

The procedure was analogous to Example 1. Instead of the methyltriphenyl phosphonium chloride, the equivalent amount of triphenylphosphine was employed.

COMPARISON EXAMPLE 2

The procedure was analogous to Example 1; however, no methyltriphenylphosphonium chloride was added.

The results of Example 1 and of Comparison Example 1 and Comparison Example 2 are summarized in FIG. 1. FIG. 1 shows the temperature-time curve (T/t curve) of the perchloroethylene hydrogenation according to the above examples at a conversion rate to trichloroethylene of 40% by weight.

EXAMPLE 2

The procedure was analogous to Example 1. However, methyltriphenylphosphonium bromide was employed as the phosphonium halide. The reaction likewise started at 195° C. As in Example 1, the conversion rate at this temperature remained at 40% by weight over a period of 900 hours.

EXAMPLE 3

The procedure was analogous to Example 1. However, ethyltriphenylphosphonium chloride was employed as the phosphonium halide. The reaction likewise started at 195° C. As in Example 1, the conversion rate at this temperature remained at 40% by weight over a period of 900 hours.

EXAMPLE 4

The procedure was analogous to Example 1. However, ethyltriphenylphosphonium halide. The reaction likewise started at 195° C. As in Example 1, the conversion rate at this temperature remained at 40% by weight over a period of 900 hours.

EXAMPLE 5

The procedure was analogous to Example 1. However, n-propyltriphenylphosphonium chloride was employed as the phosphonium halide. The reaction likewise started at 195° C. As in Example 1, the conversion rate at this temperature remained at 40% by weight over a period of 900 hours.

EXAMPLE 6

The procedure was analogous to Example 1. However, n-propyltriphenylphosphonium bromide was employed as the phosphonium halide. The reaction likewise started at 195° C. As in Example 1, the conversion rate at this temperature remained at 40% by weight over a period of 900 hours.

EXAMPLE 7

The procedure was analogous to Example 1. However, allyltriphenylphosphonium chloride was employed as the phosphonium halide. The reaction likewise started at 195° C. As in Example 1, the conversion rate at this temperature remained at 40% by weight over a period of 900 hours.

EXAMPLE 8

The procedure was analogous to Example 1. However, allytriphenylphosphonium bromide was employed as the phosphonium halide. The reaction likewise started at 195° C. As in Example 1, the conversion rate at this temperature remained at 40% by weight over a period of 900 hours.

EXAMPLE 9

The procedure was analogous to Example 1. However, n-butyltriphenylphosphonium chloride was employed at the phosphonium halide. The reaction likewise started at 195° C. As in Example 1, the conversion rate at this temperature remained at 40% by weight over a period of 900 hours.

EXAMPLE 10

The procedure was analogous to Example 1. However, n-butyltriphenylphosphonium bromide was employed as the phosphonium halide. The reaction likewise started at 195° C. As in Example 1, the conversion rate at this temperature remained at 40% by weight over a period of 900 hours.

We claim:

1. A process for the preparation of trichloroethylene comprising reacting perchlorethylene and hydrogen in the presence of a supported catalyst at a temperature of [150°-200°] *150° to 250°* C. and a hydrogen pressure 1 to 10 bar absolute, said catalyst consisting of a support of active charcoal having a BET surface area of more than 500 $m^2/g$, impregnated with 0.5 to 20% by weight of copper in elemental or chemically bonded form, 0.01 to 1.0% by weight of rhodium or palladium in elemental or chemically bonded form and 0.1 to 10.0% by weight of a water-soluble phosphonium halide, said weight based on the total weight of catalyst support and active components.

2. The process of claim 1, wherein the water-soluble phosphonium compound is selected from compounds of the formula $(Ph_3PR)X$, in which Ph represents a phenyl radical; R is selected from the group consisting of hydrogen, a substituted or unsubstituted alkyl radical and a substituted or unsubstituted aryl radical; and X is selected from the group consisting of chloride, bromide and iodide.

3. The process of claim 2, wherein R is a methyl or ethyl radical.

4. The process of claim 1 wherein the water-soluble phosphonium halide is selected from the group consisting of methyltriphenylphosphonium chloride, methyltriphenylphosphonium bromide, ethyltriphenylphosphonium chloride and ethyltriphenylphosphonium bromide.

5. The process of claim 1 wherein the amount of the water-soluble phosphonium halide compound is from 3.0 to 7.0% by weight.

6. The process of claim 1 wherein the support of active charcoal has a particle size of from 2 to 10 mm.

7. The process of claim 1 wherein the copper is present as a water-soluble copper compound.

8. The process of claim 7 wherein the water-soluble copper compound is copper (II) chloride.

9. The process of claim 1 wherein the amount of copper is from 50 to 150% by weight in elemental of chemically bonded form.

10. The process of claim 1 wherein the rhodium or palladium is present as a water-soluble rhodium or palladium compound.

11. The process of claim 10 wherein the rhodium and palladium water-soluble compound is selected from the group consisting of rhodium (II) chloride and palladium (II) chloride.

12. The process of claim 1 wherein the amount of the rhodium or palladium is from 0.02 to 0.2 percent by weight.

* * * * *